United States Patent [19]

Shaw

[11] Patent Number: 4,859,803

[45] Date of Patent: Aug. 22, 1989

[54] PREPARATION OF BISPHENOLS

[75] Inventor: Paul V. Shaw, Houston, Tex.

[73] Assignee: Shell Oil Company, Houston, Tex.

[21] Appl. No.: 194,659

[22] Filed: May 16, 1988

[51] Int. Cl.$^4$ .............................................. C07C 39/16
[52] U.S. Cl. ..................................... 568/727; 568/728
[58] Field of Search ................................. 568/727, 728

[56] References Cited

U.S. PATENT DOCUMENTS 2,730,552  1/1956  Williamson .......................... 260/619

FOREIGN PATENT DOCUMENTS 0045959  2/1987  European Pat. Off. ............. 568/727
2733537  2/1978  Fed. Rep. of Germany ...... 568/727
1185102  3/1970  United Kingdom .
1410750  10/1975  United Kingdom ................ 568/727

OTHER PUBLICATIONS

Hougen et al. "Chemical Process Principles", p. 1032 Chapter XX1 Lines 10–12, Part Three TP155 H65 C.4.

*Primary Examiner*—Werren B. Lone

[57] ABSTRACT

A process for the preparation of bisphenols which comprises treating a phenol with a ketone in the presence of a cation exchange resin catalyst and a mercaptan co-catalyst in a reactor or a series of reactors wherein all of the phenol and a portion of the mercaptan is injected into the beginning of the reactor or the first reactor and the remaining mercaptan is injected along the reactor length or in the subsequent reactors whereby cyclic dimers formation is reduced.

9 Claims, No Drawings

PREPARATION OF BISPHENOLS

FIELD OF THE INVENTION

The present invention relates to the preparation of bisphenols in the presence of ion-exchange resin catalysts using staged mercaptan co-catalyst addition to reduce the formation of cyclic dimers.

BACKGROUND OF THE INVENTION

Many processes are known to prepare bisphenols. In some of these processes, a phenol is reacted with a ketone to form the bisphenol. The reaction usually takes place in the presence of an acidic medium including inorganic acids and acidic cation exchange resins. In some cases a mercaptan, such as methyl mercaptan is used as a co-catalyst.

U.S. Pat. No. 2,730,552 describes the preparation of bisphenols in the presence of an inorganic mineral acid and a mercaptan co-catalyst. In such a process where the reactors are traditionally back-mixed, the water concentration is always high throughout the process.

However, in a process, such as described in British Pat. No. 1,185,102, which uses an ion-exchange resin catalyst, the reactor configuration is practically limited to a plug-flow reactor or a series of plug-flow reactors in which the activity of the ion-exchange resin catalyst is adversely affected by water formed in the reaction and therefore activity decreases sharply as the process progresses. Cyclic dimers by-product is a problem in such a process where mercaptan is added to increase the rate of reaction to achieve practical reaction rates when using an ion-exchange resin catalyst.

SUMMARY OF THE INVENTION

The present invention is directed to a process for the preparation of bisphenols which comprises treating a phenol with a ketone in the presence of a cation exchange resin catalyst and a mercaptan co-catalyst in a reactor or a series of reactors wherein all of the phenol and a portion of the mercaptan is injected into the beginning of the reactor or the first reactor and the remaining mercaptan is injected along the reactor length or in the subsequent reactors whereby cyclic dimers formation is reduced.

The process of staged mercaptan addition of the invention is based on applicants' discovery that in cation exchange resin catalyzed preparation of bisphenols, little mercaptan co-catalyst is needed at the beginning of the reaction, where in the presence of low water concentrations it adversely effects the formation of undesirable cyclic dimers CDA, 1,3,3-trimethyl-6-hydroxy-3-(p-hydroxy) phenylindane, and CDB, 1,3,3-trimethyl-5-hydroxy-3-(p-hydroxy)phenylidane. By the present process of limiting the amount of mercaptan at the beginning of the reaction, where water concentration is low, the formation of undesired cyclic dimers is significantly reduced.

The bisphenols prepared by the process of the invention include those prepared by the reaction of a ketone, such as acetone, ethyl methyl ketone, isobutyl methyl ketone, acetophenone, cyclohexanone, 1,3-dichloroacetone and the like, with a phenol, such as phenol, o-cresol, m-cresol, o-chlorophenol, m-chlorophenol, o-t-butylphenol, 2,5-xylenol, 2,5-di-t-butylphenol o-phenylphenol and the like. The above is not meant to limit the invention but to illustrate representative examples of ketones and phenols which are known in the art to make desirable bisphenol and for which those of skill in the art can substitute other conventional bisphenol reactants.

In the preparation of the bisphenols, an excess of the phenol is usually desirable, generally from about 5 to about 20 moles of phenol per mole of ketone, is desirable for high conversion of the ketone. Solvents or diluents are not necessary in the preparation of the bisphenol except at low temperature.

The ketone is usually introduced in stages such that from about 25–75% weight of the ketone is injected into the beginning of the reactor or the first reactor, preferably from about 40–50% weight.

The catalysts for the process are acidic cation exchange resins. Such resins which can be used as catalysts are conventionally known in the art and include those acidic cation exchange resins that are unmodified with a mercapto modifying agent before use in the process, but which are used with the addition of a free mercaptan co-catalyst. The resin is essentially not modified to any substantial degree with the free mercaptan. The free mercaptan can be any free mercaptan of the type conventionally known in the art which includes any compound which will not react to any substantial degree under the process conditions with the acidic groups of the cation exchange resin to introduce a mercaptan substituent into the resin. Suitable mercaptan co-catalyst include those of the formula RSH in which R is hydrogen or an organic group such as aliphatic, cycloaliphatic, aryl or heterocyclic compounds containing one or more free mercaptan groups. For convenience, the mercaptan usually is a non-resinous compound containing from about 1–20 carbon atoms. The mercaptan can contain other substituent groups, such as alkoxy, aryloxy, carboxy, hydroxy and the like to give simple alkyl mercaptans, mercapto acids and the like. For example, the free mercaptans include methyl mercaptan, dithioethane, ethyl mercaptan, n-pentyl mercaptan, thioglycolic acid, 1,2-dimercapto ethane, 3-mercaptopropionic acid and the like. Alkyl mercaptans are preferred, especially methyl mercaptan. The amount of mercaptan present can vary with the resin used but is usually present in a lesser amount compared to the resin. For example, the mercaptan is present from about 1 mole percent to about 100 mole percent based on the resin and preferably from about 5 to about 50 moles percent.

The amount of mercaptan co-catalyst injected into the beginning of the reactor or the first reactor is from about 30–60% weight of the total mercaptan to be used, preferably from about 40–50% weight. The mercaptan can be injected with the ketone or separately. The remainder is added after the ketone fed to the first stage or earlier stage is substantially converted to the desired bisphenol.

The effectiveness of the resin catalysts in the process of the invention is to some extent influenced by their exchange capacities such that the greater the exchange capacity then the more desirable the resin is for the condensation. Preferably, the cation exchange capacity is at least about 0.5 and, preferably, greater than 4.0 meq/g dry weight. Also, those cation exchange resins having bound cationic exchange groups of the stronger exchange potential acids are preferred for use in the resin and free mercaptan co-catalyst process of the present invention. Acidic cation exchange resins suitable for use with a free mercaptan co-catalyst include sulfonated styrene-divinylbenzene copolymers, sulfonated crosslinked styrene polymers, phenol-formaldehyde-sulfonic acid resins, benzene-formaldehyde-sulfonic acid resins and the like. These include resins under such tradenames as Amberlites (Rohm and Haas Co.), DOWEX ® (Dow Chemical Co.), Permutit QH (Permutit CO.), CHempro (Chemical Process Co,), Lewatit (Bayer A.G.) and the like. Strong acid sulfonated styrene-divinylbenzene copolymers are preferred. Both modified macroreticular resins and microreticular resins are useful in the isomerization process of the present invention. The choice of resin will of course depend on the bisphenol material to be prepared, the reaction conditions and the effect of an individual resin under the conditions selected, which determination and selection is within the skill of the art. When the aromatic sulfonic acid resins are obtained as sodium salts, they are converted to the acid from prior to use.

The precise amount of acidic cation exchange resin to be used will vary to some degree depending on the specific resin, feed and conditions used for the process. By way of illustration, the catalyst can be present from about 0.05 lbs per lb of feed per hour to about 10.0 lbs per lb of feed per hour and, preferably, from 0.2 lbs per about 2 lbs per lb of feed per hour.

Thus, the reaction is conducted by contacting a feed stream containing a phenol with an acidic cationic exchange resin and free mercaptan co-catalyst under moderately elevated temperatures and usually in the presence of from about 0 to about 1% of water, preferably from about 0.4 to about 0.6% of water, basis the total feed. The feed stream passes through the resin catalyst in the presence of free mercaptan for a period of time sufficient to effect formation of the bisphenol depending on the feed rate, size of the resin bed, the particular resin and co-catalyst used and the like as can readily be determined by those of skill in the art. The resulting bisphenol is then recovered. Usually the recovered product is recycled back to a zone in which the bisphenol is prepared by condensation of a ketone (acetone) and phenol.

The reaction time in the condensation depends on the reaction temperature and other reaction conditions, including whether the process is continuous or batch processing.

The condensation reaction is conducted at moderately elevated temperature of from about 50° C. to about 130° C. at ambient pressures.

The bisphenol product, e.g., bisphenol-A, is passed to a concentrator where the acetone, phenol, and free mercaptan and excess water are removed as an overhead fraction. The crude bisphenol-A product is then passed to a crystallization zone where it is chilled to about 30° C. to about 95° C. to form an adduct of phenol and bisphenol-A which separates out as crystals. After washing with phenol, filtering and the like, the bisphenol-A is recovered from the adduct.

As previously stated, the reactors are usually plug-flow reactors conventionally known in the art or equivalent kinds of reactors.

ILLUSTRATIVE EMBODIMENTS

The following embodiments are provided for illustration purposes and should not be regarded as limiting the invention in any way.

Embodiment 1—Production of Bisphenol A (BPA)

Two plug flow, adiabatic reactors containing Dow MSC-1 acidic ion-exchange resin were operated in series at an overall phenol to acetone mole ratio of 10. Acetone was staged by dividing it equally between the two reactors.

The mixed feed temperature was 62° C. for both reactor stages. Table 1 below compares results obtained when one-half percent by weight of reaction product of methylmercaptan co-catalyst was added with the acetone feed to the first reactor to results obtained when the same total amount of mercaptan feed was divided equally between the two reactors.

TABLE 1

| Mercaptan Staged | No | Yes |
| --- | --- | --- |
| % w Water in Feed | .1 | .1 |
| WHSV in Reactor 1 | 3.3 | 3.3 |
| WHSV in Reactor 2 | 1.6 | 1.6 |
| Overall Conversion of Acetone | 98% | 98% |
| Cyclic Dimers, ppm on BPA | 5400 | 3700 |

WHSV "means" weight hourly space velocity.

This experiment demonstrates that cyclic dimer production is reduced significantly by the staged mercaptan addition process of the present invention.

Embodiment 2—Production of Bisphenol A (BPA)

Following procedures similar to those described in Embodiment 1 above, staged and unstaged mercaptan addition was conducted with a feed water concentraion of 0.1%w (case 1) and 0.5% w (case 2). Results are set forth in Table 2 below.

TABLE 2

| Comparison of Staged to Unstaged Mercaptan | | | | |
| --- | --- | --- | --- | --- |
| | Case 1 | | Case 2 | |
| | Staged | Unstaged | Staged | Unstaged |
| Feed Water Content, % w | 0.1 | 0.1 | 0.5 | 0.5 |
| Feed Temperature, °C. | 62 | 62 | 62 | 62 |
| Reactor 1 WHSV | 3.3 | 3.3 | 3.3 | 3.3 |
| Reactor 2 WHSV | 1.6 | 1.6 | 1.05 | 1.05 |
| Conversion 1 | 0.97 | 1 | 0.8 | 0.94 |
| Conversion 2 | 0.96 | 0.96 | 0.97 | 0.96 |
| CDA 1 | 3579 | 6358 | 2064 | 3328 |
| CDA 2 | 2609 | 2609 | 2575 | 2374 |
| CDA Overall | 3081 | 4484 | 2378 | 2826 |
| CDB | 616 | 897 | 476 | 565 |
| Total CDs | 3698 | 5380 | 2854 | 3391 |
| Ratio CDs | 1 | 1.46 | — | 1.19 |
| Ratio Conversion | 1 | 1 | — | — |

WHSV "means" weight hourly space velocity.
CDA "means" 1,3,3-trimethyl-6-hydroxy-3-(p-hydroxy)phenylidane.
CDB "means" 1,3,3-trimethyl-5-hydroxy-3-(O—hydroxy)phenylidane.

These experiments demonstrate that cyclic dimer production is reduced significantly by the staged mercaptan addition process of the present invention.

What is claimed is:

1. A process for the preparation of bisphenols which comprises treating an excess of a phenol with a ketone in the presence of an effective amount of a cation exchange resin catalyst and a mercaptan co-catalyst in a reactor or a series of reactors at about 50° C. to about 130° C. at about ambient pressure, wherein all of the phenol and a portion of the mercaptan is injected into the beginning of the reactor or the first reactor and the remaining mercaptan is injected along the reactor length or in the subsequent reactors whereby cyclic dimers formation is required.

2. A process according to claim 1 wherein the co-catalyst is an alkyl mercaptan.

3. A process according to claim 2 wherein the co-catalyst is methyl mercaptan or n-pentyl mercaptan.

4. A process according to claim 1 wherein the acid is an acidic cation exchange resin.

5. A process according to claim 4 wherein the resin is selected from sulfonated styrene-divinylbenzene copolymers, sulfonated cross-linked styrene polymers, phenol-formaldehyde-sulfonic acid resins, or benzene-formaldehyde-sulfonic acid resins.

6. A process according to claim 5 wherein the resin is a sulfonated styrene-divinylbenzene copolymer.

7. A process according to claim 6 wherein the resin is a macroreticular resin.

8. A process according to claim 6 wherein the resin is a microreticular resin.

9. A process according to claim 1 for the preparation of bisphenol-A.

* * * * *

UNITED STATES PATENT AND TRADEMARK OFFICE
CERTIFICATE OF CORRECTION

PATENT NO. : 4,859,803
DATED : August 22, 1989
INVENTOR(S) : Paul V. Shaw

It is certified that error appears in the above-identified patent and that said Letters Patent is hereby corrected as shown below:

Claim 1, line 10, change "required" to -- reduced --.

Signed and Sealed this

Eleventh Day of December, 1990

Attest:

HARRY F. MANBECK, JR.

*Attesting Officer*      *Commissioner of Patents and Trademarks*